United States Patent
Coignet

(10) Patent No.: US 7,282,203 B2
(45) Date of Patent: Oct. 16, 2007

(54) USE OF NOTCH PATHWAY INTERFERING AGENTS FOR TREATMENT OF PLASMA CELL DISORDERS

(75) Inventor: Lionel J. Coignet, Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 10/996,651

(22) Filed: Nov. 24, 2004

(65) Prior Publication Data

US 2005/0129686 A1 Jun. 16, 2005

Related U.S. Application Data

(60) Provisional application No. 60/567,469, filed on May 3, 2004, provisional application No. 60/525,212, filed on Nov. 26, 2003.

(51) Int. Cl.
*A61K 39/395* (2006.01)
*C07K 16/00* (2006.01)

(52) U.S. Cl. .............. 424/130.1; 424/141.1; 424/135.1; 424/138.1; 424/139.1; 530/388.1

(58) Field of Classification Search ............. None
See application file for complete search history.

(56) References Cited

U.S. PATENT DOCUMENTS

| | | | |
|---|---|---|---|
| 6,083,904 | A | 7/2000 | Artavanis-Tsakonas |
| 6,291,210 | B1 | 9/2001 | Sakano et al. |
| 6,689,744 | B2 | 2/2004 | Gao et al. |
| 6,716,974 | B1 | 4/2004 | Maciag et al. |
| 2001/0048930 | A1 | 12/2001 | Lamb et al. |
| 2003/0185829 | A1* | 10/2003 | Koller et al. ............ 424/155.1 |

FOREIGN PATENT DOCUMENTS

WO WO 2004/076682 A2 9/2004

OTHER PUBLICATIONS

De Vos et al., Blood, 2001, vol. 98(3), pp. 771-780.*
Gaiger, et al.; Identification of Genes Associated with Multiple Myeloma and Monoclonal Gammopathy of Undetermined Significance Using the Myeloma Microarray; European Journal of Cancer, Pergamon Press; Nov. 21, 2002, vol. 38, Paragraph 344; XP-002383846; p. S103.
Luo, et al.; Isolation and Functional Analysis of a cDNA for Human *Jagged2*, a Gene Encoding a Ligand for the Notch1 Receptor; Molecular and Cellular Biology, American Society for Microbiology; Washington, US; Oct. 1997; vol. 17, No. 10; XP-000938415; pp. 6057-6067.
Felli, et al.; Expression Pattern of Notch1, 2 and 3 and Jagged1 and 2 in Lymphoid and Stromal Thymus Components; Distinct Ligand—Receptor Interactions in Intrathymic T Cell Development; International Immunology, vol. 11, No. 77; XP-002384016; pp. 1017-1025, Jul. 1999.
Almeida, et al.; Immunophenotypic and DNA Content Characteristics of Plasma Cells in Multiple Myeloma and Monoclonal Gammopathy of Undetermined Significance; Pathologie et Biologie, L'Expansion Scientifique Francaise, Paris, FR; Feb. 1999, vol. 47, No. 2; XP-009067443; pp. 119-127.
Houde, et al.; Overexpression of the NOTCH Ligand JAG2 in Malignant Plasma Cells From Multiple Myeloma Patients and Cell Lines; Blood, Dec. 1, 2004, vol. 104, No. 12; XP-002380593; pp. 3697-3704.
Gray, et al.; Human Ligands of the Notch Receptor; American Journal of Pathology; Mar. 1999, vol. 154, No. 3; XP-000960906; pp. 785-794.

* cited by examiner

*Primary Examiner*—Eileen B. O'Hara
*Assistant Examiner*—Xiaozhen Xie
(74) *Attorney, Agent, or Firm*—Hodgson Russ LLP

(57) ABSTRACT

The present invention provides a method for reducing the severity of, or treatment of, plasma cell disorders. The method comprises the step of administering to an individual afflicted with a plasma cell disorder, a composition comprising an antibody directed to the extracellular portion of NOTCH or to JAG2.

4 Claims, 12 Drawing Sheets

USE OF NOTCH PATHWAY INTERFERING AGENTS FOR TREATMENT OF PLASMA CELL DISORDERS

This application claims priority to U.S. Provisional application No. 60/525,212 filed on Nov. 26, 2003 and U.S. Provisional application No. 60/567,469 filed on May 3, 2004, the disclosures of which are incorporated herein by reference.

BACKGROUND OF THE INVENTION

Multiple myeloma (MM) is the second most frequent blood disorder in the United States. Some 13,000 new cases are diagnosed each year. MM is a clonal plasma cell proliferative disease that affects terminally differentiated B cells (i.e. plasma cells). Despite some advances in chemotherapeutic regimens, this disease remains incurable, with a median survival for MM patients of 40 months. Like MM, Monoclonal Gammopathy of Unknown Significance (MGUS) is characterized by monoclonal immunoglobulin in the serum and urine and an increase of monoclonal plasma cells in the bone marrow. However, MGUS patients do not suffer from the clinical manifestations of MM. Importantly, 25% of patients with MGUS progress to myeloma.

It is considered that the cytokine interleukin-6 (IL-6) is a major cytokine that promotes the proliferation of malignant plasma cells in MM. Elevated IL-6 levels are directly correlated with tumor burden, bone destruction, and other tumor-associated activities in myeloma patients (6) suggesting a role for IL-6 in MM. Moreover, some studies have shown that myeloma cells induce IL-6 expression in stromal cells in a largely cell-contact-dependent manner (7). Therefore, the increased levels of IL-6 production likely reflect disease-associated alteration of IL-6 regulation.

The IL-6 gene can be regulated by a variety of factors, including cytokines, IL-1, TNFalpha and, as recently demonstrated, by the NOTCH genes products. The NOTCH genes were originally identified in *Drosophila melanogaster* and are members of an evolutionarily conserved family of transmembrane receptors that help to determine cell fate during development (8). In both vertebrates and invertebrates, NOTCH genes are expressed throughout the embryonal development in uncommitted or pre-committed proliferative cells (8). During fetal and adult development, expression of NOTCH continues in the proliferative layers of mature tissues (9,10).

The fully processed NOTCH receptors consist of an extracellular sub-unit ($N^{EC}$) that is non-covalently bound to a transmembrane subunit ($N^{TM}$) which includes the cytoplasmic domain ($N^{IC}$). The N-terminal sequence of $N^{IC}$ contains the high-affinity interaction site for the transcription factor CBF1/RBP-Jkappa (11), which can regulate the IL-6 gene. Ligand-induced cleavage of the transmembrane subunit has been demonstrated in *Drosophila* and mammalian cells. This cleavage releases the entire intracellular portion of NOTCH which enters the nucleus and can interact with transcription factors such as CBF1 (FIG. 1).

Despite all the efforts by several teams/investigators to develop effective treatment for MM, this disease remains incurable. The treatments that are used in this disease allowed only limited efficacy in treating the disease. Conventional chemotherapy, mainly Melphalan, has been used extensively in the past, but when compared with allogeneic bone marrow transplantation (ABMT), only 14% of the patients reached complete remission (CR) as compared with ABMT with 38%. When high-dose chemotherapy is used, 22-30% CR is achieved. When combined with total body irradiation, 43% of CR and very good partial response is achieved. New therapeutic approaches are tested nowadays but they are all in phase I/II state. These compounds are Thalidomide and its derivatives (IMIs), protease inhibitor PS341-Velcade and Arsenic trioxide. However, the disease remains incurable. Available trials for some IMIds and PS341 show 71% (but only 13% of the patient showed a >75% reduction of paraprotein) and 47% (but only 30% of the patient showed a >75% reduction of paraprotein) of CR/PR, respectively. Accordingly, new approaches are needed for more effective treatment of plasma cell disorders.

SUMMARY OF THE INVENTION

The present invention provides a method for novel therapeutic approaches to the treatment of plasma cell disorders. The method comprises the use of agents which interfere with the NOTCH pathway.

In one embodiment, the invention provides a method for reducing the severity of plasma cell disorders or treatment of plasma cell disorders comprising the steps of administering antibodies to NOTCH protein, particularly the extracellular portion of the NOTCH1 protein.

In another embodiment, the invention provides a method for reducing the severity of plasma cell disorders or treatment of plasma cell disorders comprising the steps of administering antibodies to JAG2 protein. The JAG2 protein is a surface protein considered to be on malignant plasma cells.

In another embodiment, the invention provides a method for reducing the severity of plasma cell disorders or treating plasma cell disorders comprising the steps of administering antibodies to NOTCH protein and/or antibodies to the JAG2 protein in combination with a cytotoxic agent. An example of a useful chemotherapeutic agent is doxorubicin.

BRIEF DESCRIPTION OF THE FIGURES

FIG. 5A shows IL-6 assay by ELISA on various co-culture conditions with either MRC5 alone, MRC5 co-cultured with K620 (MM) alone or with incremental amount of anti-NOTCH1 Mab A6 (5, 10, 15, 20, 40 μg). The IL-6 secretion was observed to be inversely proportional to the amount of Mab used. FIG. 5B shows another experiment in which IL-6 secretion was measured for MRC5 cells alone, MRC5 cells co-cultured with MM cells, RPMI8226, and MRC5 cells co-cultured with RPMI8226 in the presence of an anti-JAG2 antibody (M8).

FIG. 6B shows data for another group which also has a mouse that was not treated.

In FIG. 7A, data is shown for IL-6 secretion for MRC5 cells alone, MRC5 cells with K620 cells (MM cells) without an insert (marked "alone") and with an insert. In FIG. 7B, data is also shown for VEGF secretion for MRC5 cells alone, RPMI8226 cells (MM) alone, U26 cells (MM) alone, MRC5 cells with RPMI8226 and MRC5 with U226.

In FIG. 11B, $IC_{50}$ data is shown for OPM2 cells on fibroblast with 0.1 M DOX, an isotype antibody or an anti-NOTCH-EC antibody. In FIG. 11C, data is shown for the effect of the anti-NOTCH antibody alone, without DOX. In FIG. 11D, $IC_{50}$ values are shown for OMP2 cells incubated alone, in the presence of DOX or in the presence of DOX with an anti-JAG2 antibody (M8).

DESCRIPTION OF THE INVENTION

Figure 1:
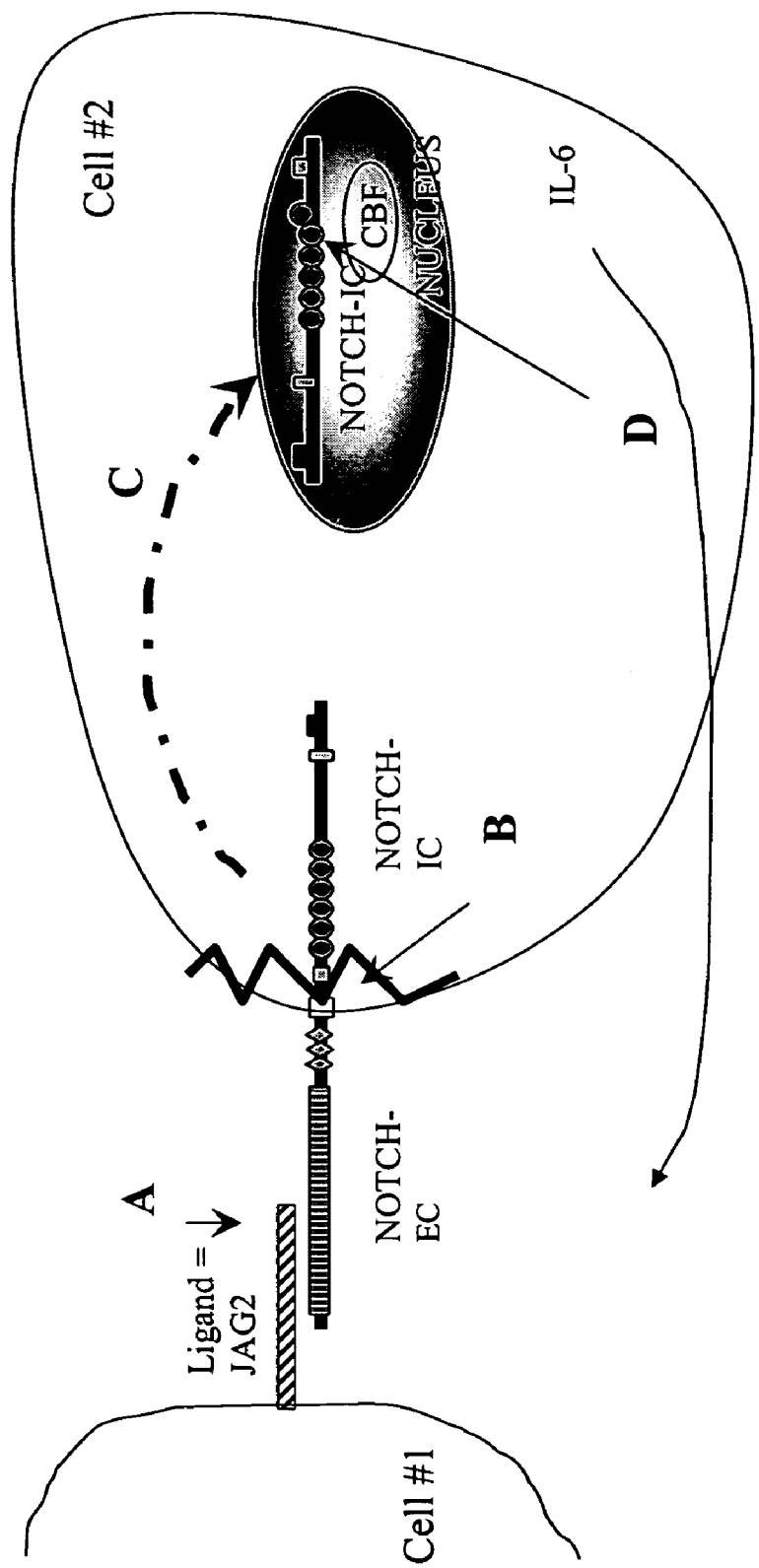
FIG. 1. Schematic representation of the physiological activation of NOTCH, with Cell #1 (MM cell) expressing JAG2 and cell #2 (such as a stromal cell) expressing NOTCH. A: JAG2 binds NOTCH via cell-to-cell contact. B: Binding of JAG2 induces a proteolytic cleavage of the intracellular part of NOTCH (NOTCH-IC). C: Once cleaved, NOTCH-IC is translocated into the nucleus. D: Once in the nucleus, NOTCH-IC is be able to bind to downstream effectors such as CBF1, to activate, for example, the IL-6 gene transcription.
Figure 2:
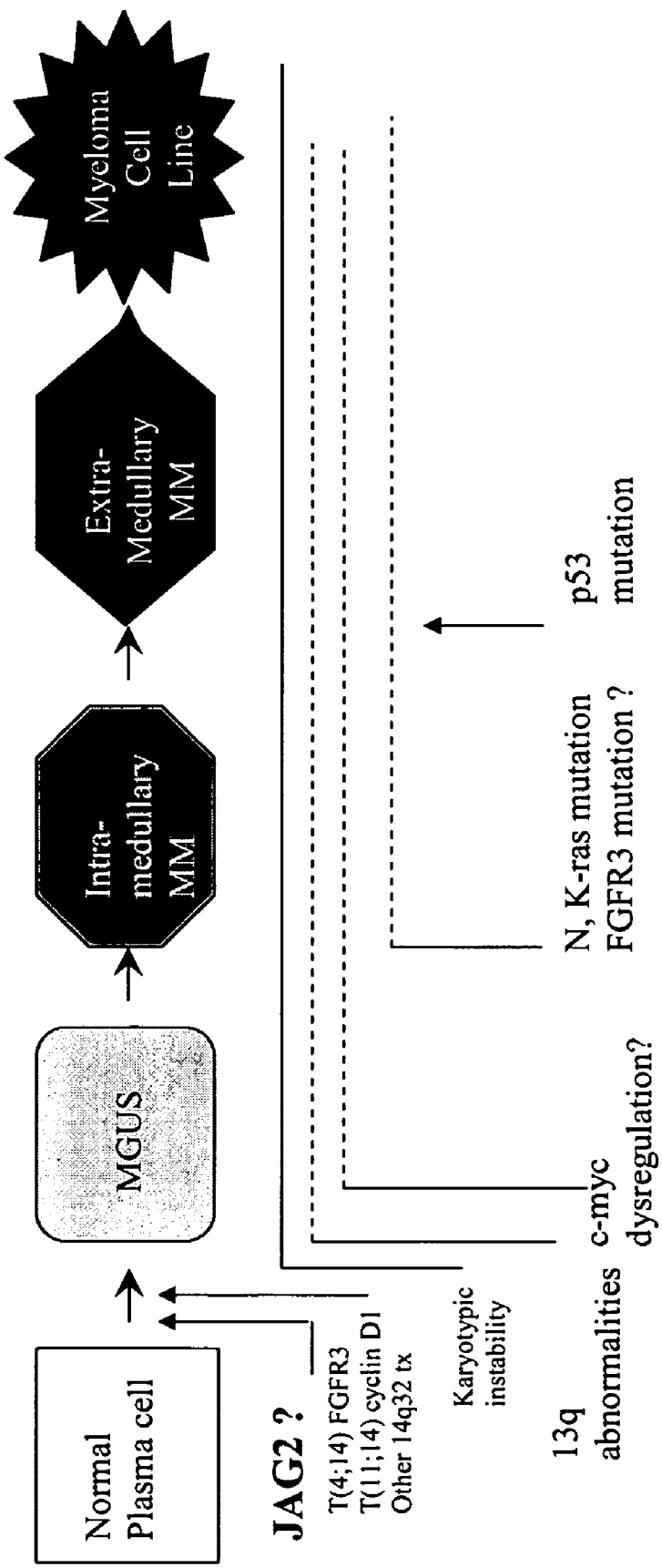
FIG. 2. Progressive genetic events in MM. Although not every stage is discernible in each patient, there appears to be an ordered progression from a normal plasma cell; to MGUS where the cells are immortalized, but not transformed, and do not progressively accumulate or cause bone destruction; to intra-medullary myeloma, where the cells are confined to the bone marrow (BM) micro-environment, accumulate and cause bone destruction; to extra-medullary myeloma, where the cells proliferate more rapidly and grow in the blood (plasma cell leukemia) or other extra-medullary sites; to a myeloma cell line, where the cells may be propagated in vitro. This model summarizes the possible timing of genetic events in relation to clinical progression.
Figure 3:
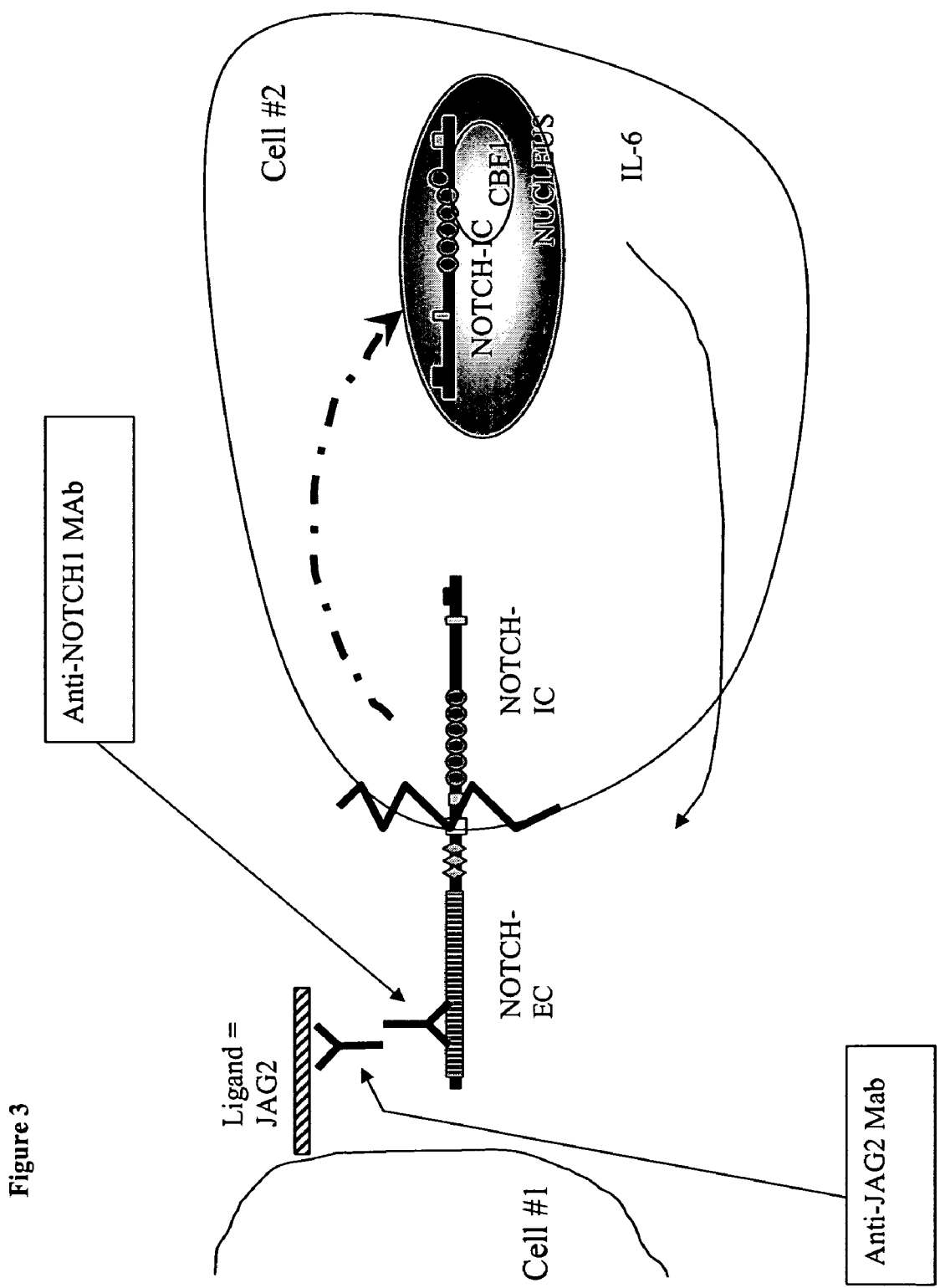
FIG. 3. Schematic representation of the sites of action of the reagents we tested in order to block the NOTCH pathway and activation of NOTCH. The anti-NOTCH1 monoclonal antibody is directed against the NOTCH1 binding peptide which is involved in the binding to JAG2. The anti-JAG2 monoclonal antibody is directed against the JAG2 binding peptide that is involved in the binding of NOTCH1

The present invention provides methods for reducing the severity of, or treatment of, plasma cell disorders, such as MGUS and MM. In one embodiment, reduction in severity of, or treatment of, a plasma cell disorder is measured as the reduction in the level of Ig produced by the malignant plasma cells. The method comprises interfering with the NOTCH pathway. This includes interference with or blocking of the NOTCH-JAG2 pathway and/or inactivation of NOTCH activation by any other means. Accordingly, included in the present invention are reagents that interfere with any stage of the NOTCH pathway, resulting in the blocking of the NOTCH protein activation. In one embodiment, the interfering agents are targeted to the extracellular components of this pathway. Similarly, agents that interfere with the intracellular action of NOTCH can also be used The NOTCH pathway is shown in FIG. 1. This pathway can be interfered with at several sites. Our data indicates that over-expression of the NOTCH ligand, JAG2, may play a causative role in the development of plasmacytosis, giving rise to MGUS and/or to the propagation of fully malignant plasma cells in MM (FIG. 2). JAG2 over-expression activates NOTCH, which drives the secretion and release of IL-6 in the micro-environment supporting myeloma cells growth. Thus, an example of some potential sites for interference with the NOTCH-JAG2 pathway, are shown in FIG. 3. In one embodiment, agents, which interfere with the binding of NOTCH 1 to JAG2, such as antibodies directed against JAG2 or NOTCH, can be used. In general all agents of the present invention aim at blocking the activation of the NOTCH protein i.e. the translocation of the NOTCH IC into the nucleus (FIG. 3).

In one embodiment, the agent for interfering with the NOTCH pathway is an antibody directed to the extracellular portion of NOTCH (also referred to herein as "NOTCH-EC"). Thus, this antibody can be used for reducing the severity of plasma cell disorders, or treatment of plasma cell disorders. Similarly, in another embodiment, the agent for interfering with the NOTCH pathway is an antibody to JAG2 protein.

In another embodiment, the invention provides a method for reducing the severity of plasma cell disorders or treating plasma cell disorders comprising the steps of administering antibodies to NOTCH protein and/or antibodies to the JAG2 protein in combination with a chemotherapeutic agent. An example of a useful chemotherapeutic agent is doxorubicin.

The antibodies of the present invention may be polyclonal, monoclonal, or antibody fragments e.g., single chain Fv, Fab', F(ab')$_2$ etc., that specifically bind JAG2 or the extracellular portion of NOTCH protein such that the NOTCH pathway activation is inhibited.

Polyclonal antibodies directed to JAG2 or the NOTCH EC can be prepared by immunizing a suitable subject with the protein. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and *corynebacterium parvum*. The antibody titer in the immunized subject can be monitored over time by standard techniques, such as with an enzyme linked immunosorbent assay (ELISA) using immobilized proteins. If desired, the antibody molecules directed against JAG2 or the NOTCH EC peptide can be isolated from the mammal (e.g., from the blood) and fiuther purified by well known techniques, such as protein A chromatography to obtain the IgG fraction.

Monoclonal antibodies directed toward JAG2 or the NOTCH EC can also be produced by standard techniques. Briefly, an immortal cell line (typically a myeloma) is fused to lymphocytes (typically splenocytes) from a mammal immunized with a JAG2 or the NOTCH EC, and the culture supernatants of the resulting hybridoma cells are screened to identify a hybridoma producing a monoclonal antibody that binds JAG2 or the NOTCH EC. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind JAG2 or the NOTCH EC, e.g., using a standard ELISA assay. Human hybridomas can be prepared in a similar way.

An alternative to preparing monoclonal antibody-secreting hybridomas is to identify and isolate monoclonal antibodies by screening a recombinant combinatorial immunoglobulin library (e.g., an antibody phage display library) with JAG2 or the NOTCH-EC.

Antigen binding fragment of antibodies can also be used. An example is single chain antibody fragments, i.e., scFv. These usually comprises the entire antigen binding site and are the smallest antibody fragment that retains specific binding characteristics. scFv are produced by randomly connecting the variable heavy ($V_H$) and variable light ($V_L$) chain immunoglobulin genes together using a biologically inert flexible linker. While scFv molecules can be produced from existing monoclonal antibodies, phage display libraries now provide a multitude of scFv from a single source, allowing those with optimal binding characteristics to be simultaneously selected along with the genes encoding the displayed scFv (1. Pavlinkova et al. (1999) J Nucl Med, 40:1536-1546; Viti et al. (1999) Cancer Res, 59: 347-352; Winter et al. (1994)Annu. Rev. Immunol, 12: 433-455; Clackson et al. (1991) Nature, 352: 624-628; Hoogenboom et al. (1998) Immunotechnology, 4: 1-20; Phage display of peptides and proteins: a laboratory manual. San Diego: Academic Press, 1996).

In one embodiment, a method is provided for reducing the severity of or treatment of plasma cell disorders. The method comprises administering an antibody or antibody fragment, which specifically binds to the JAG2 protein or the NOTCH EC in amounts that are sufficient to reduce the severity of the plasma cell disorder. The antibodies or antibody fragments can be administered in pharmaceutically acceptable formulations that are well within the purview of those skilled in the art. The NOTCH pathway interfering agents of the present invention can be administered by any standard means known in the art. In one embodiment, the agents are administered by intravenous route in suitable pharmaceutical carriers. These antibodies are useful in reducing the levels of circulating Ig that is produced by the malignant plasma cells. Therefore, one way of monitoring the effect of an antibody against NOTCH-EC or JAG2 during treatment of a plasma cell disorder is to monitor the levels of circulating Ig that is produced by the malignant plasma cells.

The present invention also relates to the combined use of cytotoxic agents and the anti-NOTCH or anti-JAG2 antibodies. It was observed that the effects of cytotoxic agents could be observed at lower doses if administered with the antibodies of the present invention. Therefore, in one embodiment, a method of provided to reduce the dose of a chemotherapeutic agents that is required to obtain a desired effect by administration of an anti-NOTCH EC or an anti-JAG2 antibody. This may help to reduce the side effects associated with the use of cytotoxic agents. In another embodiment, a greater effect can be obtained at a given dose of the cytotoxic agent by administration of an anti-NOTCH-EC or an anti-JAG2 antibody. Current treatments for the management of multiple myeloma involves mesphalan, doxorobucin, dexamethasone, thalidomide and derivatives such as reclimid. These can be administered by standard routes either concurrently or sequentially.

This invention is described through Examples presented below which are intended to be illustrative and not restrictive in any way.

EXAMPLE 1

Figure 4:
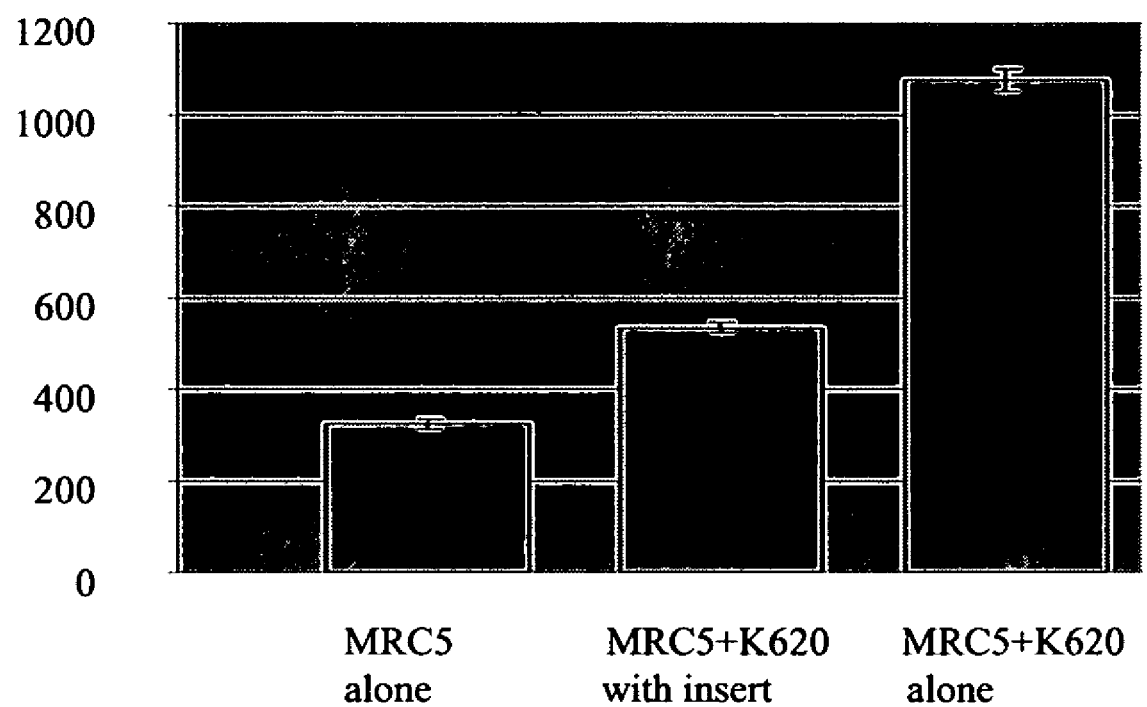
FIG. 4. IL-6 detection assay by ELISA for the assessment of IL-6 secretion upon various culture conditions. Results are shown for MRC5 alone, MRC5 co-cultured with K620 (MM) in an insert (no contact between the two cell types) and MRC5 co-cultured with K620.

This embodiment demonstrates that IL-6 secretion is elicited by MM cells. In order to demonstrate that IL-6 secretion is a direct consequence of JAG2 over-expression in the MM context, we developed a co-culture in vitro assay using fibroblast cells and our multiple myeloma cell lines (that over-express JAG2 as already shown). We used the MRC5 fibroblast cell line as a feeder layer in these experiments. Culture wells were seeded with MRC5 cells. Upon 70% confluence, the cells were irradiated to stop their growth. Culture medium was collected for MRC5 cells cultured alone, co-cultured with a MM cell line or co-cultured with a MM cell line but separated from them by an insert, avoiding cell contacts between the two cell types. IL-6 levels were assayed on the culture medium. As shown in FIG. 4, the co-culture of MRC5 and the MM cell line induced a 3.5-fold increase in IL-6 secretion whereas the same co-culture without contact between the two cell types only marginally affected IL-6 secretion underlining the need for the IL6 release and myeloma cell growth, of a direct contact with the micro-environment.

EXAMPLE 2

Figure 5A:
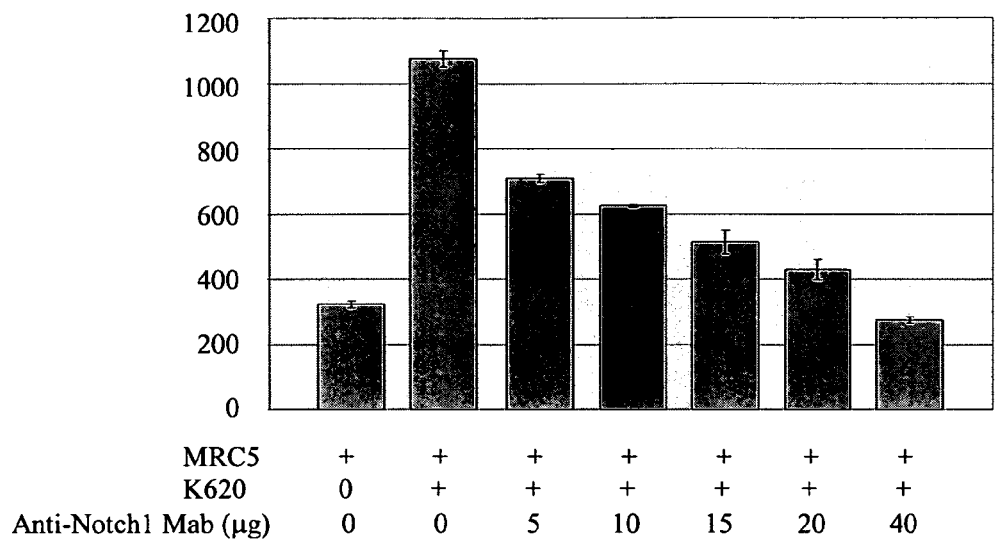
FIGS. 5A and 5B.
Figure 5B:
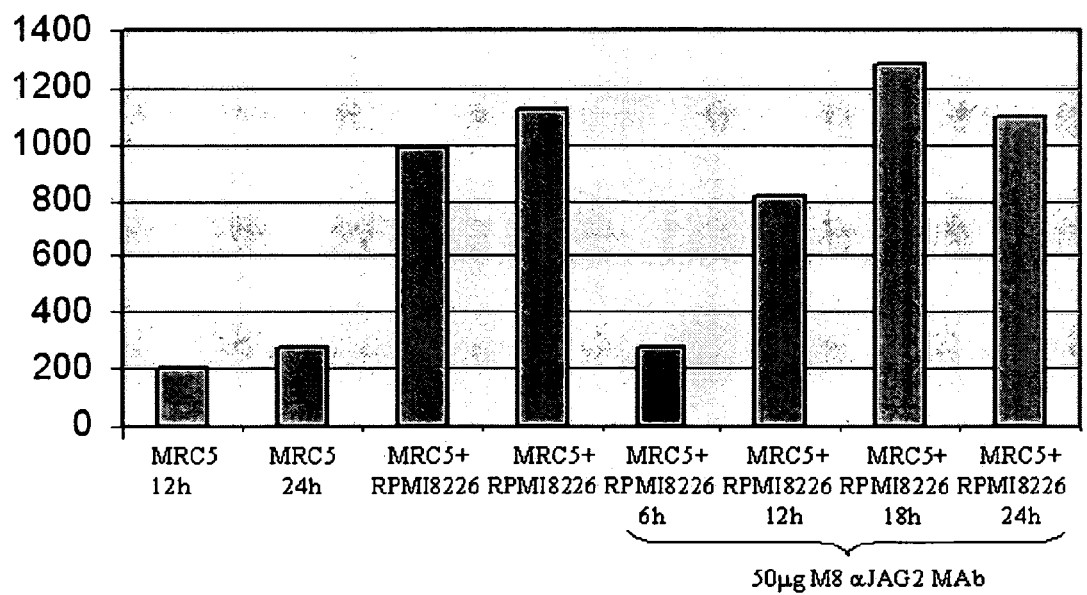

In this embodiment, an anti-NOTCH1 monoclonal antibody was used to block the NOTCH pathway. This antibody (A6) has been raised against NOTCH1 peptide and is considered to block the binding of JAG2 to NOTCH1 (FIG. 3). The assay was similar to one described in Example 1. MRC5 cells were co-cultured with the myeloma cell line in the presence of an increasing amount of anti-NOTCH1 monoclonal antibody (5, 10, 20, 40 µM). The results of these experiments (FIG. 5A) show that when the monoclonal antibody was added to the cultures, IL-6 release was reduced. Furthermore, the reduction in the IL6 release from the fibroblasts was proportional to the amount of monoclonal antibody added to the culture medium, showing that this agent was able to block the release in a specific manner. Thus, by blocking NOTCH activation, the release of IL6 induced by the contact between the 2 cell types is reduced. A similar effect of increased secretion of IL-6 was seen when MRC5 cells were co-cultured with another MM cell line, RPM18226 and when the co-cultures were incubated with an anti-JAG2 antibody (M8), the IL-6 secretion was decreased (FIG. 5B). Similarly, other antibodies directed against the peptide responsible for the binding of JAG2 to NOTCH 1, and other agents interfering with this binding can also be used. These should have the same effect as the anti-NOTCH1 Mab shown here (FIG. 3).

EXAMPLE 3

In this example, SCID mice were used to demonstrate the effect of interference with the NOTCH pathway in vivo. SCID-Hu mice were obtained as follows. 19-23 weeks old human fetal bones were obtained from the Birth Defects Laboratory, University of Washington, Seattle, Wash. These long fetal bones were implanted sub-cutaneously in CB17 SCID mice. Seven frozen MM patient samples were injected in the fetal bone from different SCID mice (after light irradiation) and levels of human Ig were monitored to assess the development of subsequent MM in the fetal bone. Mice with transplanted fetal bone but without MM sample injected were used as controls. Blood serum was obtained from the mice through-eye bleeds and Ig levels were assessed by ELISA assay. Ig was detected in five out of seven mice, corresponding to five different MM samples. In addition, we could document the bone disease induced by the proliferation of the MM in the fetal bone.

Figure 6A:
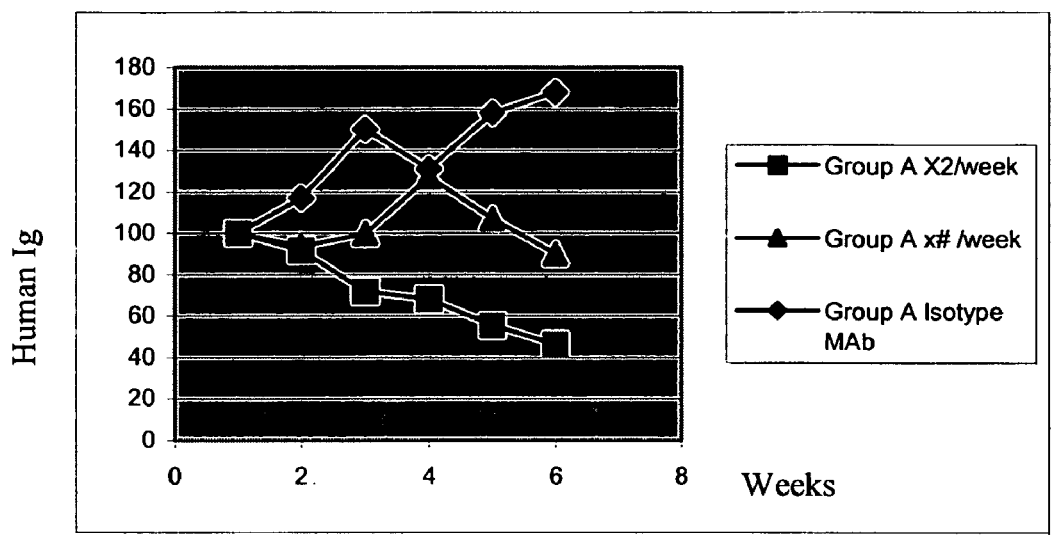
FIG. 6A and 6B. Anti-myeloma-activity of anti-NOTCH antibodies in two groups of treated mice. The X-axis shows time in weeks and the Y-axis shows level of human Ig. Data is shown in FIG. 6A for mouse treated with treated with a control antibody (isotype), mouse which received the antibody twice a week and a mouse which received the antibody three times a week.
Figure 6B:
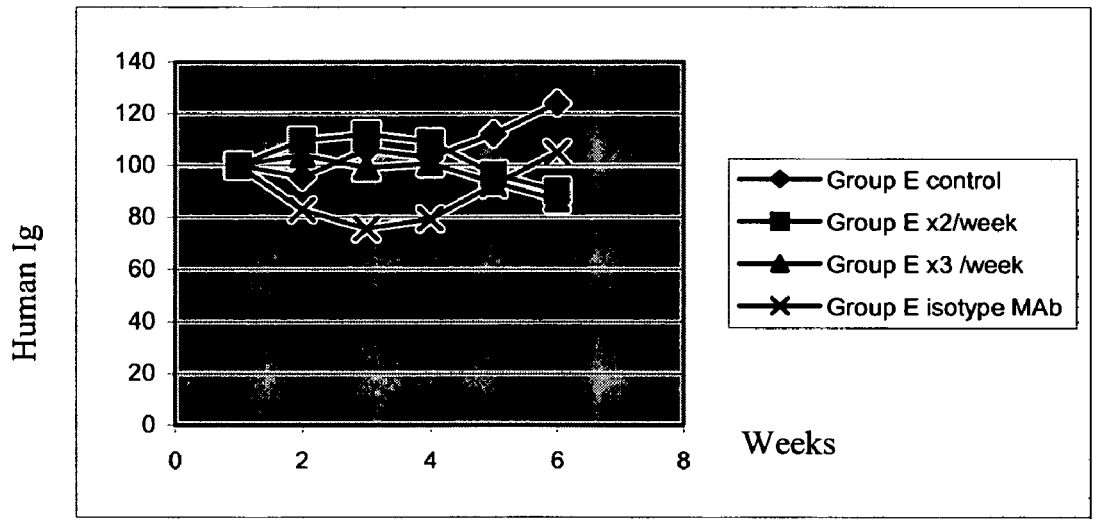

The anti-NOTCH1 MAb was used in the model described above. As shown in FIGS. 6a and 6b, the anti-NOTCH1 Mab shows anti-myeloma activity in the 2 groups of treated mice. In FIG. 6A, data is shown for one mouse treated twice a week, one treated three times a week and one treated with an isotype antibody. In FIG. 6B, data is shown for one non-treated mouse, one mouse treated twice a week, one treated three times a week and one treated with an isotype antibody. Groups A and E correspond to SCID mice injected with the bone marrow from 2 different patients. A detection of Ig in the mice is an indication of disease since the Ig is produced by the implanted MM cells.

In Group A, the isotype is rising and indicates no effect of injection of a non specific antibody. When an injection of 2×/week was made, the Ig decrease by 50% of the amount of human ig detected in the mouse blood i.e., reduction of 50% of the disease. When an injection of 3×/week was made, first increase and then decrease is observed.

In another group Group E, the control is seen to increase. However a non-specific reaction is seen here with the isotype. Both 2× and 3×/week increased slightly to decrease later. These results indicate that depending upon the particular individual, these antibodies can be used to at least stabilize the individual.

EXAMPLE 4

Figure 7A:
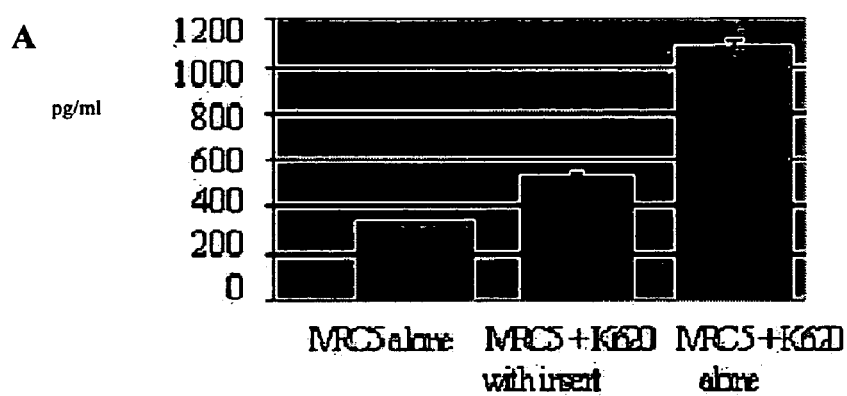
FIGS. 7A and 7B. IL-6 and VEGF secretion upon co-culture of MM cell lines and the MRC5 cell line.
Figure 7B:
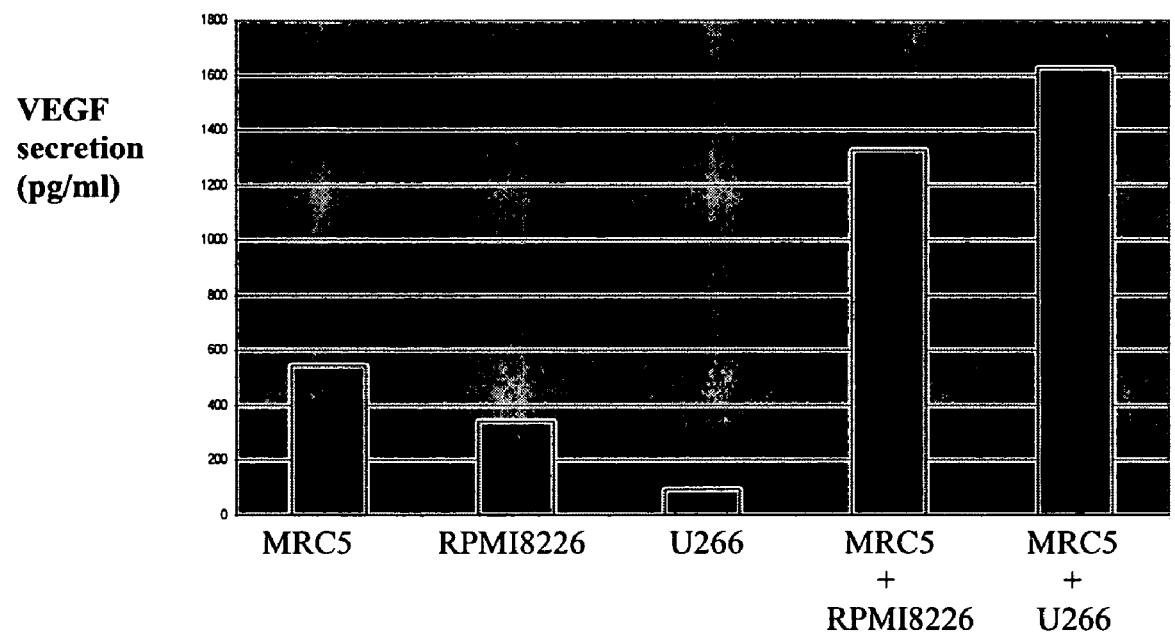

In addition to studying the release of IL-6 in our in vitro assay, we have been testing the release of VEGF and IGF-1 by the stromal cells upon cell-to-cell contact with myeloma cells. We use the MRC5 cell line as a stromal cell layer in our dishes and a myeloma cell line is co-cultured on top of the MRC5, allowing cell-to-cell contact between the 2 cell lines. These two cytokines have been shown to be key elements in the development of multiple myeloma. As shown in FIGS. 7A and 7B, we have shown that co-culture between our MRC5 cells and a MM cell line induces secretion and release of VEGF and IGF-1.

Figure 8A:
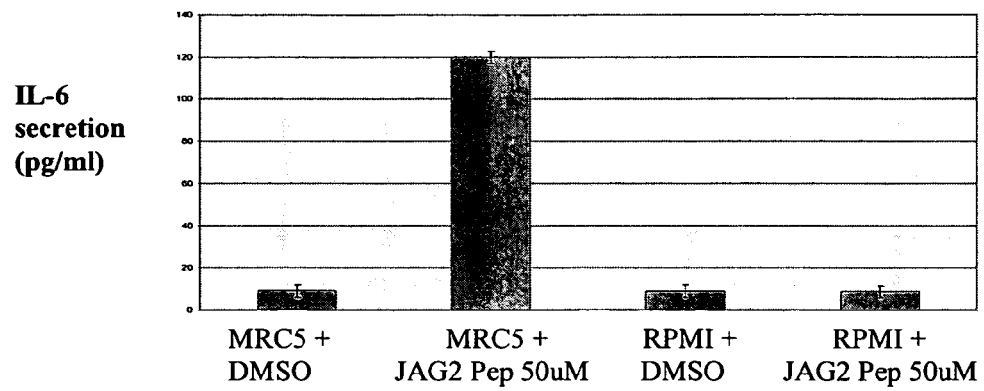
FIGS. 8A-C. Induction of the secretion of IL-6 (FIG. 8A); VEGF (FIG. 8B) and IGF-1 (FIG. 8C) by incubation of the MRC5 and RPMI8226 cell lines with a JAG2 binding peptide CDENYYSATCNKFCRPRND (SEQ ID NO:1) at the indicated concentrations.
Figure 8B:
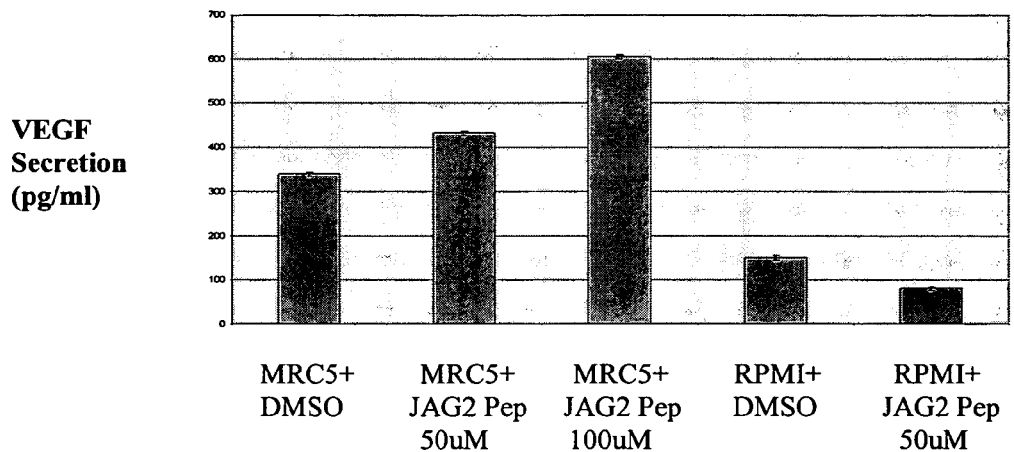
Figure 8C:
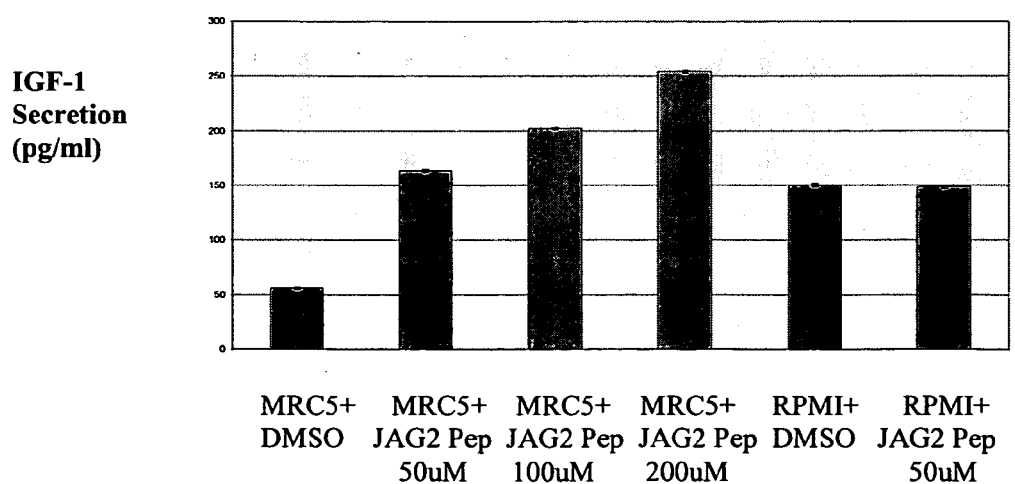

In order to ascertain the involvement of JAG2 in the induction of the secretion of IL-6, VEGF and IGF-1, we incubated the MRC5 cell line with different concentrations of JAG2 peptide. This peptide corresponds to the binding region of JAG2 that activates NOTCH upon interaction. We also incubated the RPMI8226 cell line with this same peptide. As shown in FIGS. 8A-c, the secretion of IL-6, VEGF and IGF-1 was activated by the JAG2 binding peptide when incubated with the MRC5 cell line whereas there is no stimulation when incubated with the MM cell line, in line with our induced paracrine hypothesis.

Figure 9A:
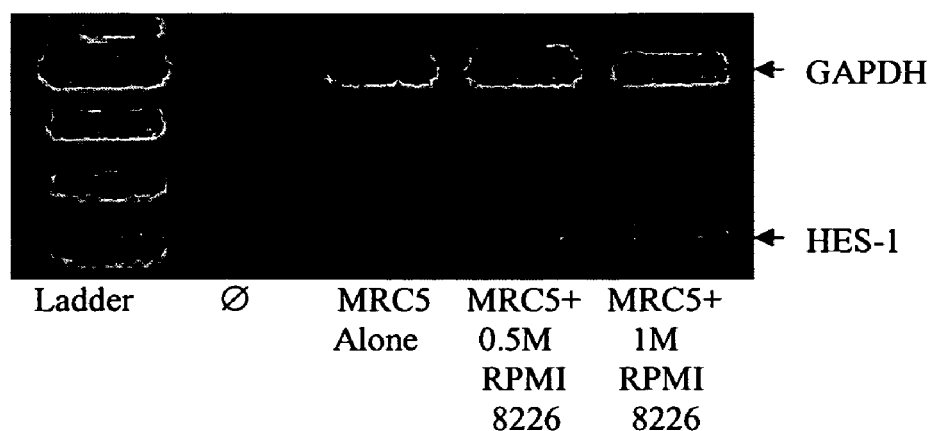
FIGS. 9A and 9B. Semi-quantitative PCR for HES-1 expression with RNA extracted from the MRC5 cells after co-culture with RPMI8226. The RT-PCR results are shown in FIG. 9A and the fold amplification of HES-1 expression for MRC5 cells alone or cultured with a MM cell line RPMI8226 is shown in FIG. 9B. 0.5M and 1.0M indicates number of cells (in millions) set in culture on top of the MRC5 cells.
Figure 9B:
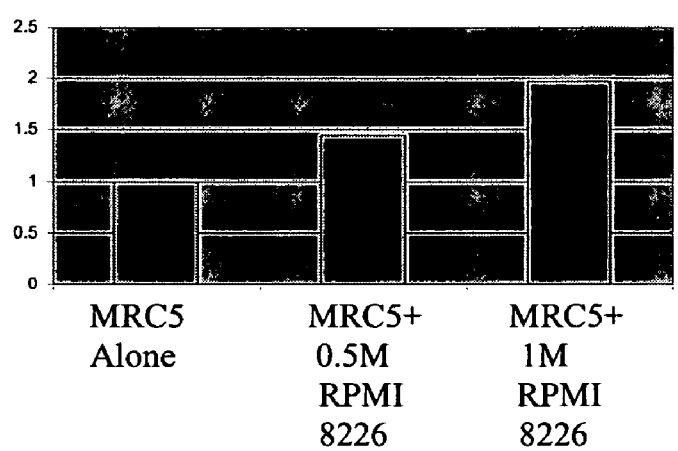
Figure 10:
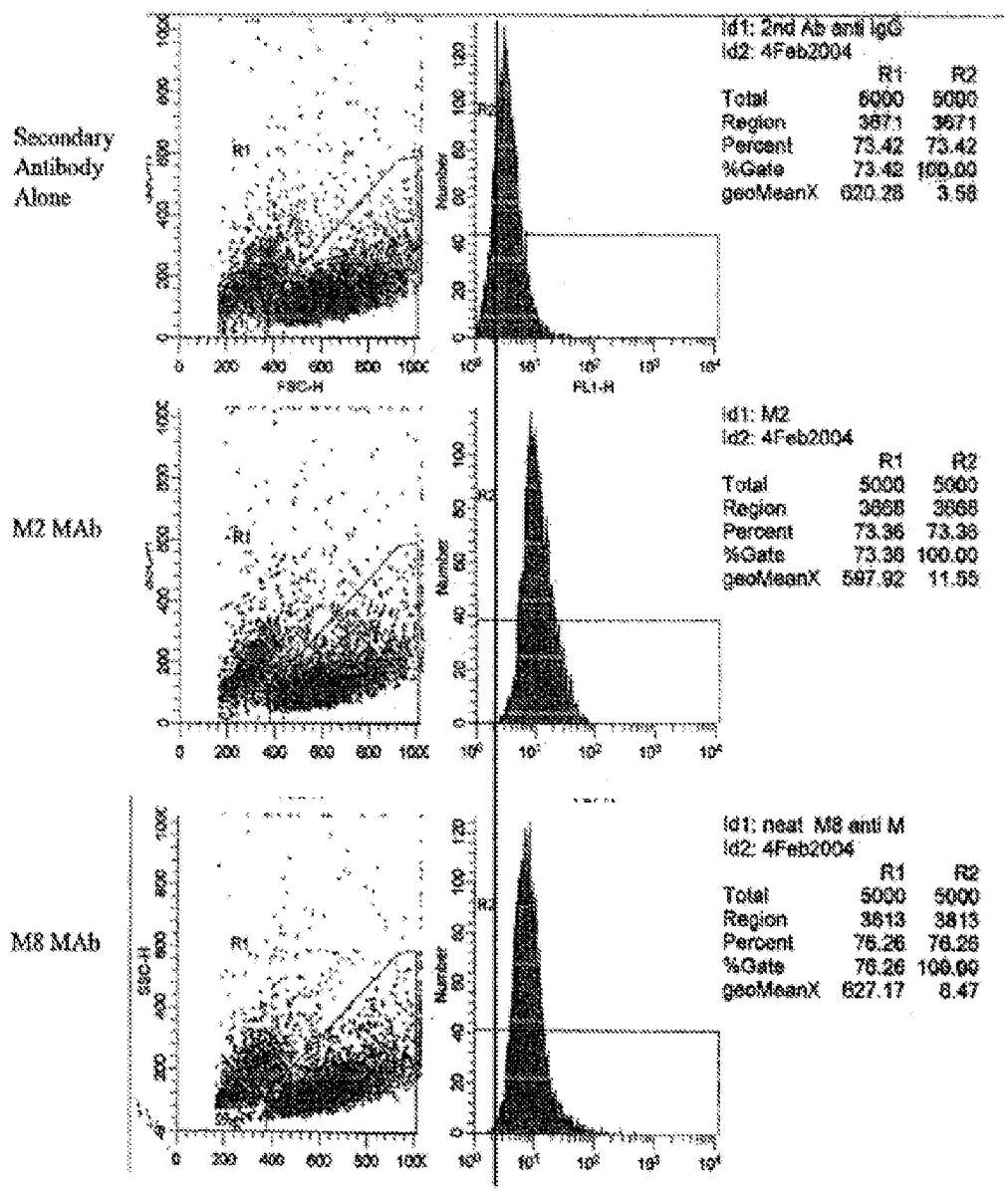
FIG. 10. FACS analysis of the RPMI8226 MM cell line with either secondary antibody alone, M2 or M8 monoclonal antibodies. The non-concentrated hybridoma supernatants were used in these experiments.

In order to test whether known NOTCH target genes are activated upon co-culture of the MRC5 cell line with a MM cell line, we established the in vitro system for 48 hours of culture. After this time of co-culture of both cell lines (MRC5 and RPMI8226), the MM cells were removed and RNA was extracted from the MRC5 cells. The RNA obtained was used in semi-quantitative RT-PCR experiments to determine the potential transcription activation of the HES-1 gene, which is a well-known and classical target of NOTCH. As shown in FIGS. 9A and 9B, the level of HES-1 transcript increased proportionally to the number of RPM18226 cells used in the co-culture, with a 1.5-fold increase when 0.5 million RPMI8226 cells were used and a 2-fold increase with 1 million RPMI8226 cells, as compared with MRC5 alone.

All of the JAG2 detections were performed using a commercially available polyclonal antibody. In addition, monoclonal antibodies useful for interference with the JAG-NOTCH pathway were also generated. We used the JAG2 binding peptide to immunize mice. The sequence of this peptide is: NH2-CDENYYSATCNKFCRPRND-OH (SEQ ID NO: 1). Briefly, JAG2 binding peptides were generated and coupled with KLH. Mice were immunized with this conjugated peptide to generate a polyclonal antibody response. Serum was collected and tested by ELISA. Spleens were removed from the animals and the cells were fused with mouse myeloma cells to create a hybridoma library. The monoclonal cultures were prepared from the hybridoma library using flow cytometry cell sorting for single viable cells. Individual cultures were tested by ELISA and supernatants were tested on our MM cell lines. We obtained 10 monoclonal hybridomas that reacted positively by ELISA. Isotyping of these clones showed 4 IgG1, 3 IgM, 1 IgA and 2 that gave mixed signals with IgM and IgG 1. Purification of 2 Mab, M8 (IgM) and M2 (IgG1) was carried out. The hybridoma that produces M8 was deposited pursuant to the Budapest Treaty reQuirements with the American Type Culture Collection (ATCC), 10801 University Boulevard, Manassas, Va., 20110, on Oct. 12, 2006, and has been assigned Patent Deposit Designation PTA-7918.

EXAMPLE 4

Figure 11A:
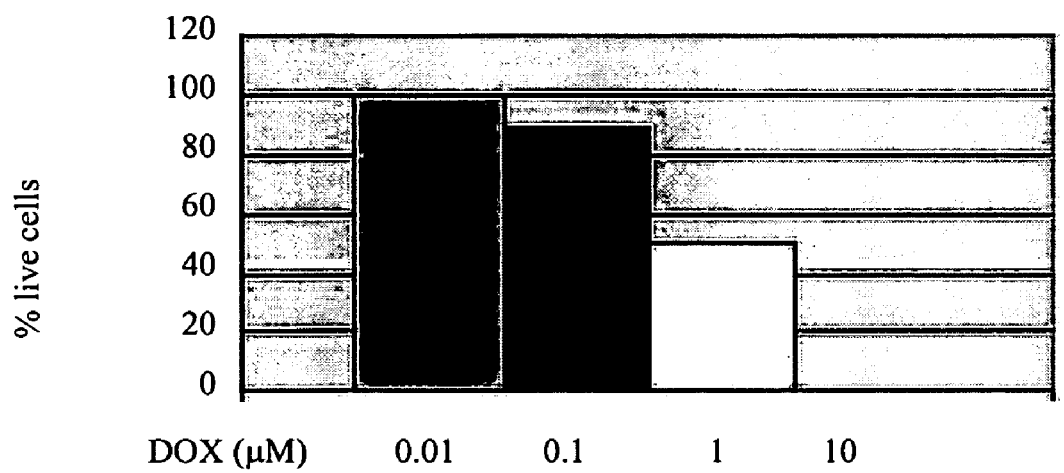
FIG. 11A-D. $IC_{50}$ for OPM2 cells (MM) incubated with doxorubicin (DOX) alone or in the presence of an anti-NOTCH or anti-JAG2 antibody. OPM2 (MM) cells were cultured on fibroblasts (MRC5) In FIG. 11 A, $IC_{50}$ data is shown for cells incubated with different concentrations of DOX.
Figure 11B:
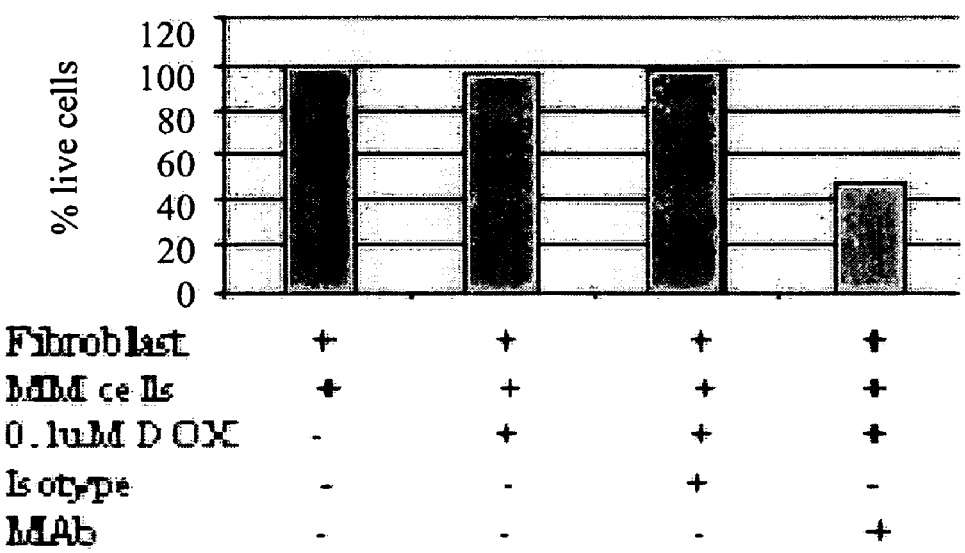
Figure 11C:
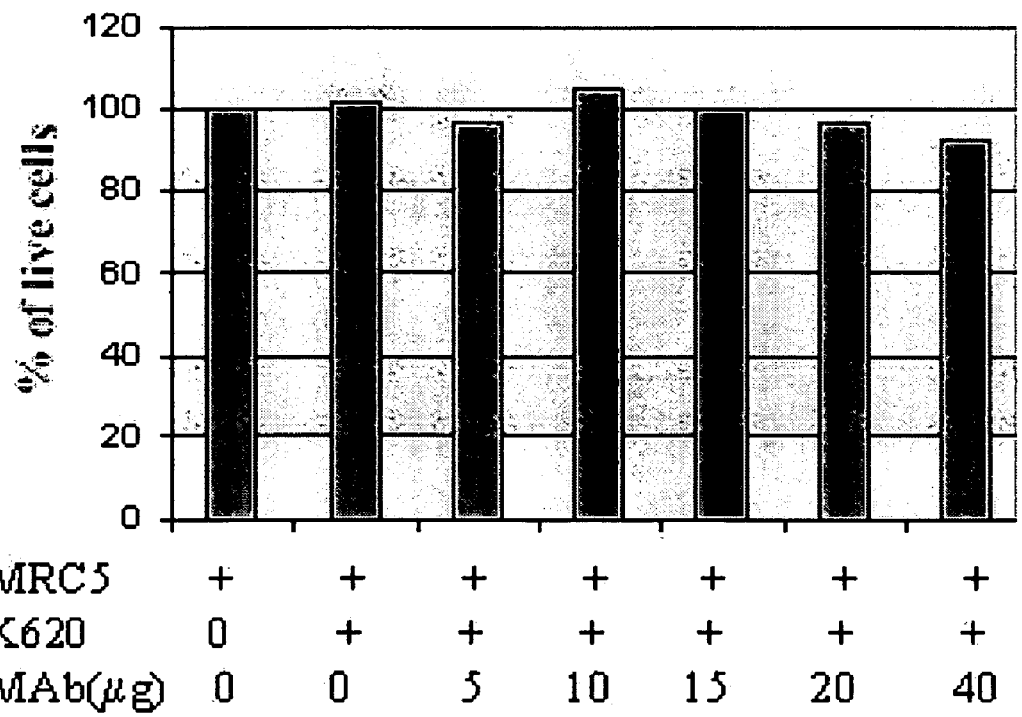
Figure 11D:
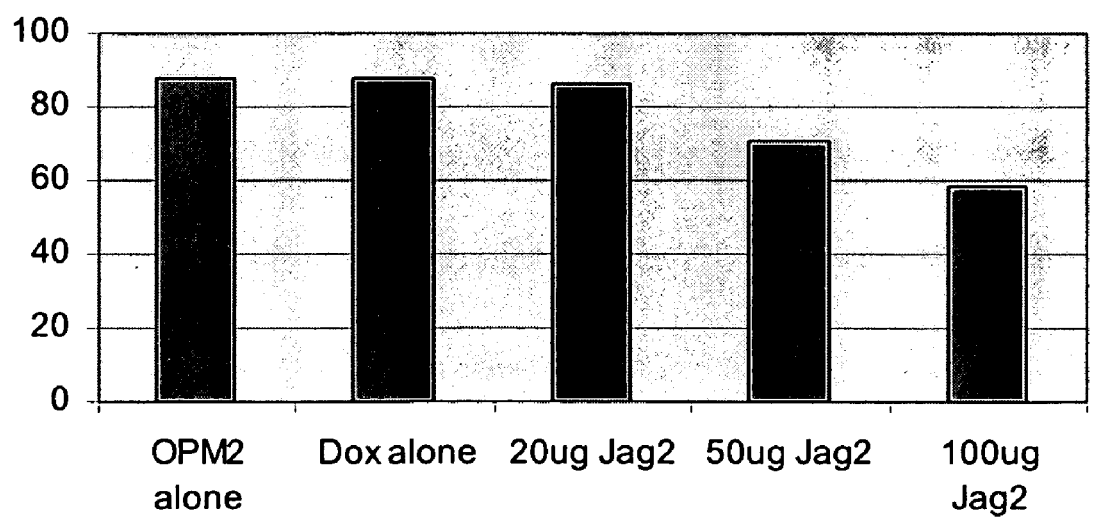

This embodiment demonstrates that the combined use of cytotoxic agents and the anti-NOTCH-EC or anti-JAG2 antibodies to produce a synergistic effect. To illustrate this embodiment, the anti-NOTCH-EC antibody or the anti-JAG2 antibody was used in combination with doxorubicin (DOX). The OPM2 MM cells were cultured for 48 hours on fibroblast cells with different concentrations of DOX. As shown in FIG. 11A, a dose dependent effect was observed on the percent of living cells (by MTT assay). An $IC_{50}$ was observed to be about 1uM. When the same experiment was carried out in the presence of 40 µg (27 µg/ml) of an anti-NOTCH EC antibody (FIG. 11B) the $IC_{50}$ was observed at almost 10 times less concentration of DOX i.e., at 0.1 µM. When the cells were incubated with the anti-NOTCH antibody alone (without DOX), no effect on killing was observed at 40 µg (FIG. 11C). Similarly, as shown in FIG. 11D, when cells were incubated with DOX alone, no effect on the percent of living cells was observed. However, when increasing concentrations of the anti-JAG2 were added, the percent of living cells was seen to decrease. Again, no effect of the anti-JAG2 antibody alone was observed at these concentrations of the antibody (data not shown). These results indicate that the anti-JAG2 or the anti-NOTCH-EC antibodies and cytotoxic agents have a synergistic effect on the killing of MM cells.

While specific embodiments are presented to illustrate this invention, routine modifications to these embodiments will be apparent to those skilled in the art and such modifications are intended to be within the scope of the invention.

REFERENCES

1. I C M MacLennan, M Drayson, J Dunn, . BMJ 1994; 308:1033-1036
2. R A Kyle. Stem Cells. 2, 56, 1995
3. S V Kajkumar, P R Greipp, Pp 1295-1315 in Hematology/Oncology clinics of North America, Kyle and Gertz, editors. Monoclonal Gammopathies and related disorders. WB Sabders editions.
4. Shelly L L, Fuchs C, Miele L, J Cell Biochem 1999 May 1;73(2):164-75.
5. Wolfe et al., J Med Chem 41, 6-9 (1998).
6. Zhang X G, Bataille R, Widjenes J, Klein B,. *Cancer.* 1992 March 15;69(6):1373-6.
7. Vidriales M B, Anderson K C., *Mol Med Today* 2: 425, 1996.
8. Artavanis-Tsakonas S, Matsuno K, Fortini ME., *Science.* 268:225-32, 1995
9. Miele L, Osborne B., J Cell Physiol 1999 December;181 (3):393-409
10. Osborne B., Miele L., *Immunity,* 11, 653-663, 1999.
11. Tamura K, Taniguchi Y. Minoguchi S, Sakai T, Tun T. Furukawa T, Honjo T., *Curr Biol.* 5:1416-23, 1995

The invention claimed is:

1. A method for treatment of, or reducing the severity of, a plasma cell disorder in an individual, wherein the disorder is selected from monoclonal gammopathy of unknown significance (MGUS), intra-medullary myeloma, extra-medullary myeloma and plasma cell leukemia, comprising the step of administering to the individual a composition comprising a monoclonal antibody or an antigen binding fragment thereof, wherein the monoclonal antibody or antigen binding fragment thereof is reactive to a peptide having the sequence of SEQ ID NO: 1, in a pharmaceutically acceptable carrier, wherein administration of the composition results in reduced circulating Ig.

2. The method of claim 1, wherein the antibody fragments are selected from the group consisting of scFv, Fab' and $F(ab')_2$.

3. The method of claim 1, wherein the plasma cell disorder is multiple myeloma or monoclonal gammopathy of unknown significance.

4. The method of claim 1, wherein the antibody is anti-JAG2 antibody M8.

* * * * *

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: synthetic JAG2 binding peptide

<400> SEQUENCE: 1

Cys Asp Glu Asn Tyr Tyr Ser Ala Thr Cys Asn Lys
            5                   10

Phe Cys Arg Pro Arg Asn Asp
        15